(12) United States Patent
Varchena (10) Patent No.: US 7,699,522 B2
(45) Date of Patent: Apr. 20, 2010

(54) FOUR-DIMENSIONAL COMPUTED TOMOGRAPHY QUALITY ASSURANCE DEVICE

(76) Inventor: Vladmir Varchena, 2301 Catamaran Ct., Virginia Beach, VA (US) 23451

( * ) Notice: Subject to any disclaimer, the term of this patent is extended or adjusted under 35 U.S.C. 154(b) by 51 days.

(21) Appl. No.: 12/290,200

(22) Filed: Oct. 28, 2008

(65) Prior Publication Data
US 2009/0225957 A1 Sep. 10, 2009

Related U.S. Application Data

(60) Provisional application No. 61/000,789, filed on Oct. 29, 2007.

(51) Int. Cl.
*G01D 18/00* (2006.01)
(52) U.S. Cl. .................................... 378/207
(58) Field of Classification Search ............ 378/4, 378/18, 65, 207
See application file for complete search history.

(56) References Cited

U.S. PATENT DOCUMENTS

2007/0195929 A1* 8/2007 Ruchala et al. ............... 378/65
2007/0201613 A1* 8/2007 Lu et al. ...................... 378/65
2008/0298540 A1* 12/2008 Serban et al. ................ 378/18

* cited by examiner

*Primary Examiner*—Irakli Kiknadze
(74) *Attorney, Agent, or Firm*—Stephen E. Clark (57) ABSTRACT

Quality assurance device for calibrating and testing the accuracy of movement-correlated computed tomography ("4D CT") target-locating systems has a test unit sub-assembly adapted to be combined with a dynamic phantom system. The test unit sub-assembly has an axially and rotationally moveable test rod slideably disposed inside of a substantially hollow fixed housing. A matrix of markers, or "fiducials", are located in the wall of the housing. A single fiducial is located near the distal end of the moveable test rod. The distal end portion of the moveable test rod is adapted to be connected to a motion actuator, which is programmed to oscillate the test rod in a predetermined pattern. When the test unit sub-assembly is inserted into a tissue equivalent phantom member, the combined sub-assembly and phantom member can then be subjected to four-dimensional imaging to generate a visual image. A visual comparison actual relative positions of the fiducials to the know positions of the fiducials in time indicates the accuracy of the 4D CT system.

10 Claims, 7 Drawing Sheets

FOUR-DIMENSIONAL COMPUTED TOMOGRAPHY QUALITY ASSURANCE DEVICE

RELATED APPLICATIONS

The present patent document claims the benefit of the filing date under 35 U.S.C. Sec. 119(e) of Provisional U.S. Patent Application Ser. No. 61/000,789, filed Oct. 29, 2007, which is hereby incorporated by reference.

BACKGROUND OF THE INVENTION

1. Field of Invention

The present invention relates generally to four-dimensional (4D) computed tomography (CT) quality assurance (QA) equipment. More particularly the present invention relates to devices used to calibrate, confirm and test the accuracy of movement-correlated 4D CT target-locating systems.

2. Description of the Prior Art

The technologies of intensity-modulated radiotherapy (IMRT) have undergone rapid change. Four-dimensional CT acquisition—that is, CT acquisition of a moving three-dimensional target object (for example, a tumor)—is commercially available, and can provide important information on the shape and trajectory of a tumor and normal tissues. The primary advantage of four-dimensional imaging over light breathing helical scans is the reduction of motion artifacts during scanning that can significantly alter tumor appearance.

Precise knowledge and control of three-dimensional dose distribution in considered to be essential for a favorable therapeutic outcome. The ability to deliver highly conformal dose distributions through intensity-modulated radiotherapy has become common for sites such as head and neck and prostate. When the target moves due, for example, to respiration, precise delivery of dose becomes more challenging.

Artifacts due to motion (known as "temporal aliasing artifacts") during tomographic scans have been appreciated for many years. Three-dimensional CT images are typically obtained by taking a series of adjacent image slices (or, alternatively, a continuous helix of images) of a subject who/that is typically placed on a platform (e.g., bed) that moves relative to the scanner, and are then digitally stitching (via computer software) the various image slices together. If the subject moves relative to the bed, as for example during breathing, while adjacent image slices are being scanned, the movement can result in temporal aliasing artifacts.

In order to minimize such temporal aliasing artifacts, motion-correlated CT systems have been proposed. Motion-correlated CT systems that acquire 3-dimensional image data are referred to herein as four-dimensional CT ("4D CT") systems.

Respiration-correlated CT uses a surrogate signal, tracking movement such as of the abdominal surface, or of respiratory air flow, or of internal anatomy to provide a signal that permits re-sorting of the reconstructed image data, resulting in multiple coherent spatiotemporal data sets at different respiratory phases. The scan time for 4DCT with multislice scanners is on the order of a few minutes. In general, in order to re-sort and correlate the image data, each image slice is time- and/or position-stamped and each surrogate signal is time- and/or position-stamped. Computer software is then used to re-sort and correlate the various image slices into the proper sequences as dictated by the time- and/or position-stamps of the respective surrogate and the image slices. The output of this process is typically 10 CT volumes, each with a temporal resolution of approximately $\frac{1}{10}^{th}$ of the respiratory period.

The ability of a 4D CT system to accurately re-sort and faithfully reconstruct three-dimensional data sets of a moving target volume within a subject depends heavily on how accurately and precisely the system can track the actual position in space of that target volume relative to the subject at all times during the scanning process.

There is a need, then, for a means to confirm, measure and calibrate the accuracy and precision with which a 4D CT system tracks the actual position in space of a scanned target volume.

SUMMARY OF THE INVENTION

The present invention is directed to a quality assurance method and apparatus, for use in conjunction with a 4D CT system, for determining the accuracy and precision to which the 4D CT system tracks the position in space of a target volume relative to the position of a scanned subject in which the target volume is located.

It is an object of the present invention to provide a quality assurance device of the character described that can be used in conjunction with CT, PET, MRI or ultrasound imaging systems.

Other features and advantages of the invention will be apparent from the following detailed description accompanying drawings.

REFERENCE NUMERALS IN DRAWINGS

D1 outside diameter (of test rod distal shoulder 16b)
D2 outside diameter (of test cylinder 14)
10 4D CT QA device, general
12 Test apparatus sub-assembly
14 Test cylinder
   14a inside surface (of test cylinder)
   14b outside surface (of test cylinder)
15 Collar (of test cylinder)
16 Test rod
   16a shaft (of test rod)
   16b distal shoulder (of test rod)
   16c proximal shoulder (of test rod)
18 Fiducial (static)
20 Fiducial (moveable)
22 Hole (in distal shoulder of test rod)
24 Counterbored hole (in proximal shoulder)

28 Holes (in test cylinder 14)
30 Opening (in phantom body)
  30a Opening (in phantom body)
32 Phantom body
33 Phantom base member
34 Assembly base member
35 Controller support fixture
38 Motion actuator assembly
40 Motion controller assembly
42 Actuator rod

DETAILED DESCRIPTION

Figure 6:
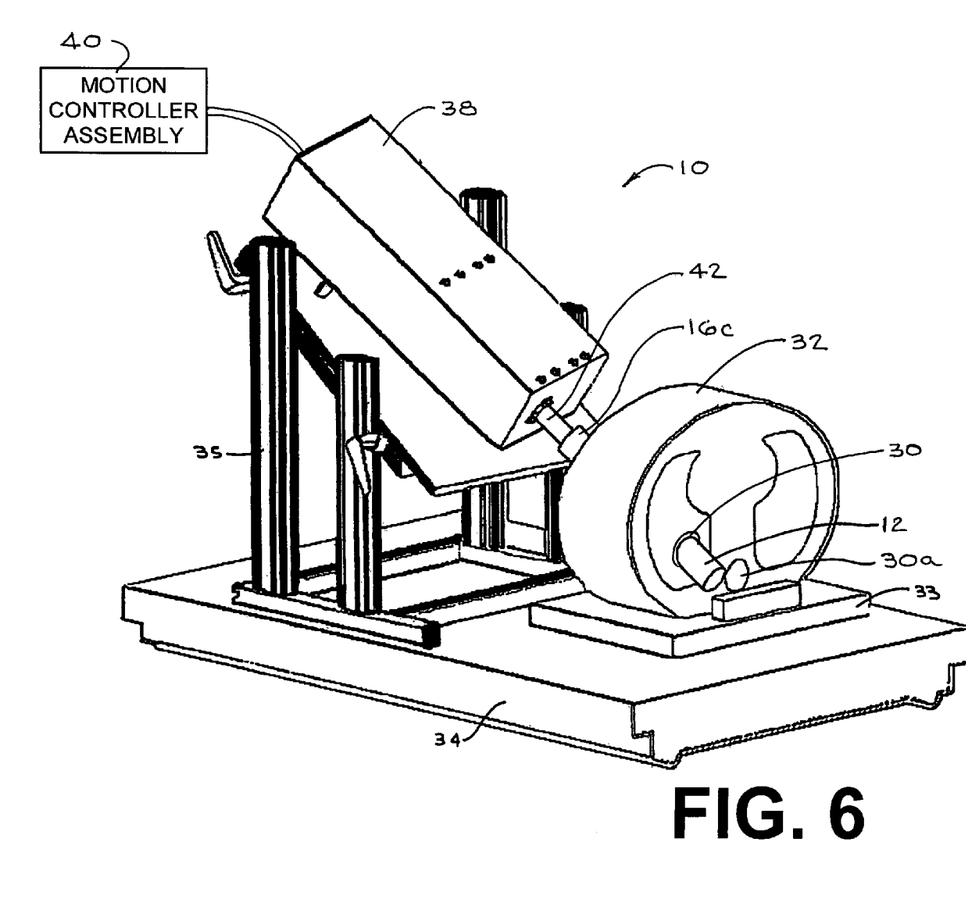
FIG. 6 is a perspective view of a 4D CT QA device constructed in accordance with the present invention.

A quality control device 10, constructed in accordance with a preferred embodiment of the present invention, is shown in FIG. 6. As will be discussed in detail below, the device, hereafter referred to as a four-dimensional computed tomography quality assurance device (or "4D CT QA device") 10, may be used in a preferred embodiment to calibrate, confirm and/or test the accuracy of motion-correlated CT systems that acquire 3-dimensional image data.

Figure 1:
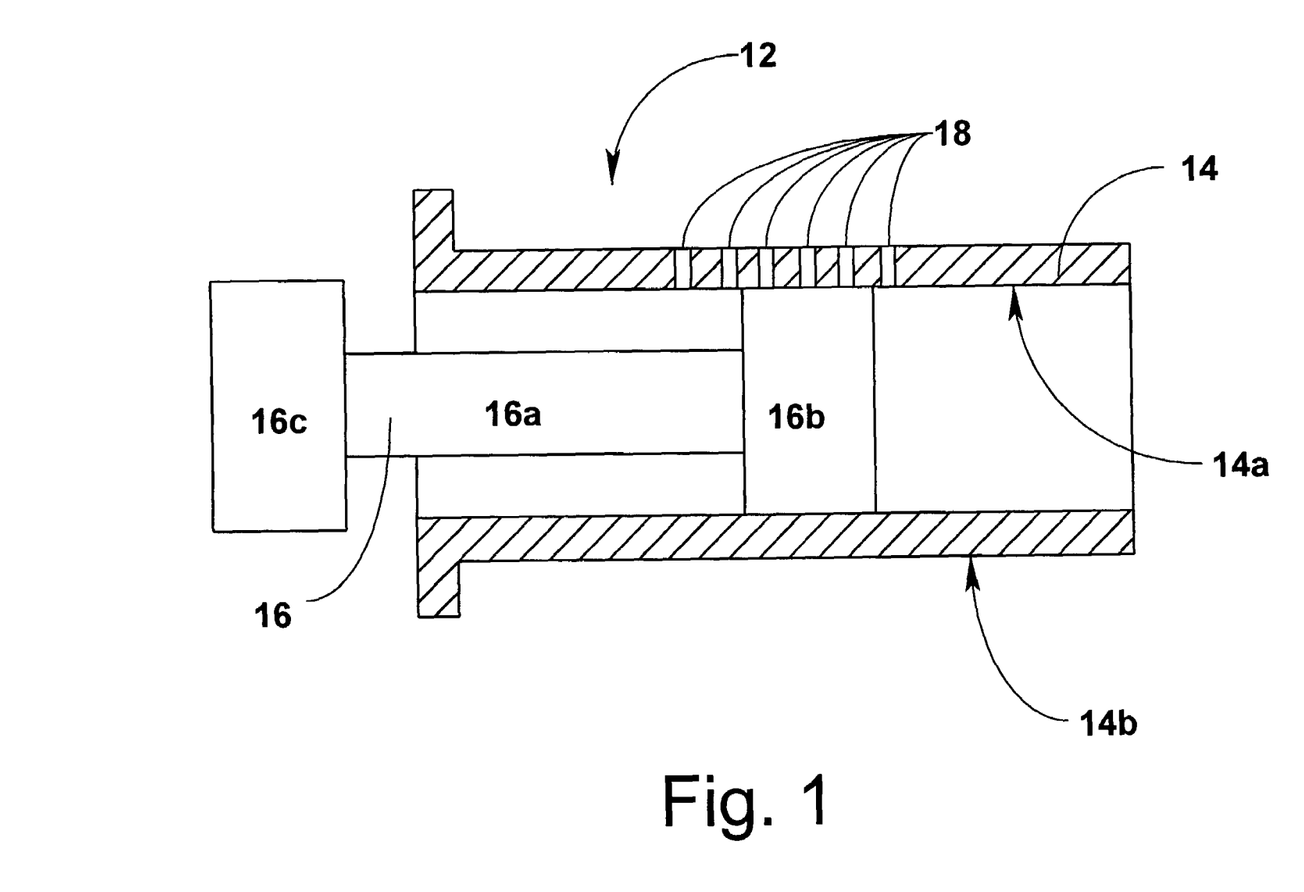
FIG. 1 is a cross-sectional view of a test rod and test cylinder sub-assembly in accordance with the present invention.

Referring to FIGS. 1 and 6: A four-dimensional computed tomography quality assurance (4D CT QA) device 10 comprises a test apparatus sub-assembly 12, which comprises a test cylinder 14 and a test rod 16, as illustrated in FIG. 1. Test rod 16 is disposed inside of test cylinder 14. Preferably, test rod 16 is both axially and rotationally moveable within test cylinder 14.

The test apparatus sub-assembly 12 has at least two sets of CT markers ("fiducials") 18 and 20, which are located in the test cylinder 14 and the test rod 16, respectively. In operation, since test rod 16 is moveable within test cylinder 14, the two sets of fiducials 18 and 20 are moveable relative to each other. More specifically, fiducials 18 are operationally static (and are, therefore, referred to herein below as "static fiducials" 18); and fiducial 20 is operationally moveable (and is, therefore, referred to herein below as the "moveable fiducial" 20).

Figure 2:
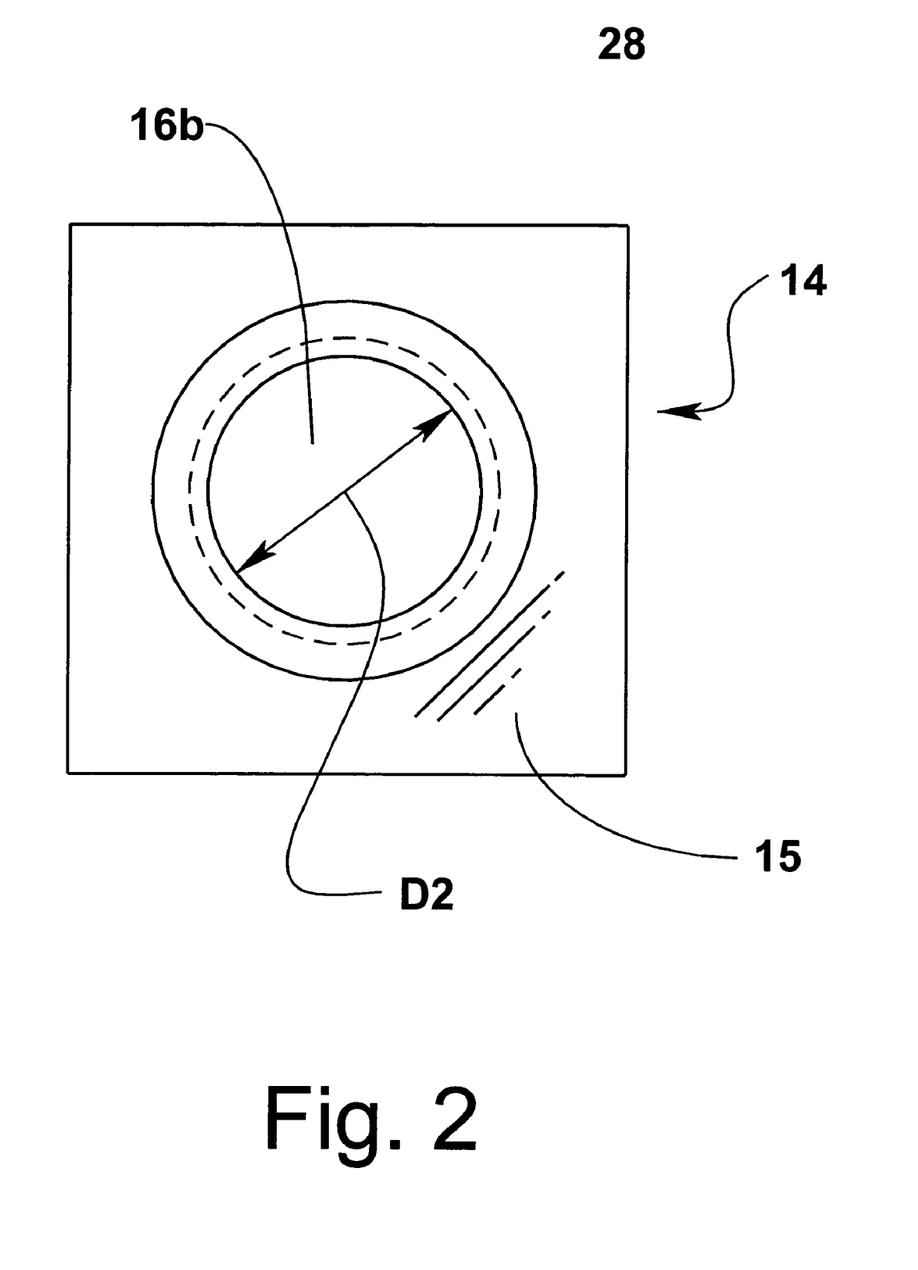
FIG. 2 is an elevation view of the front of a test cylinder constructed in accordance with the present invention.
Figure 3:
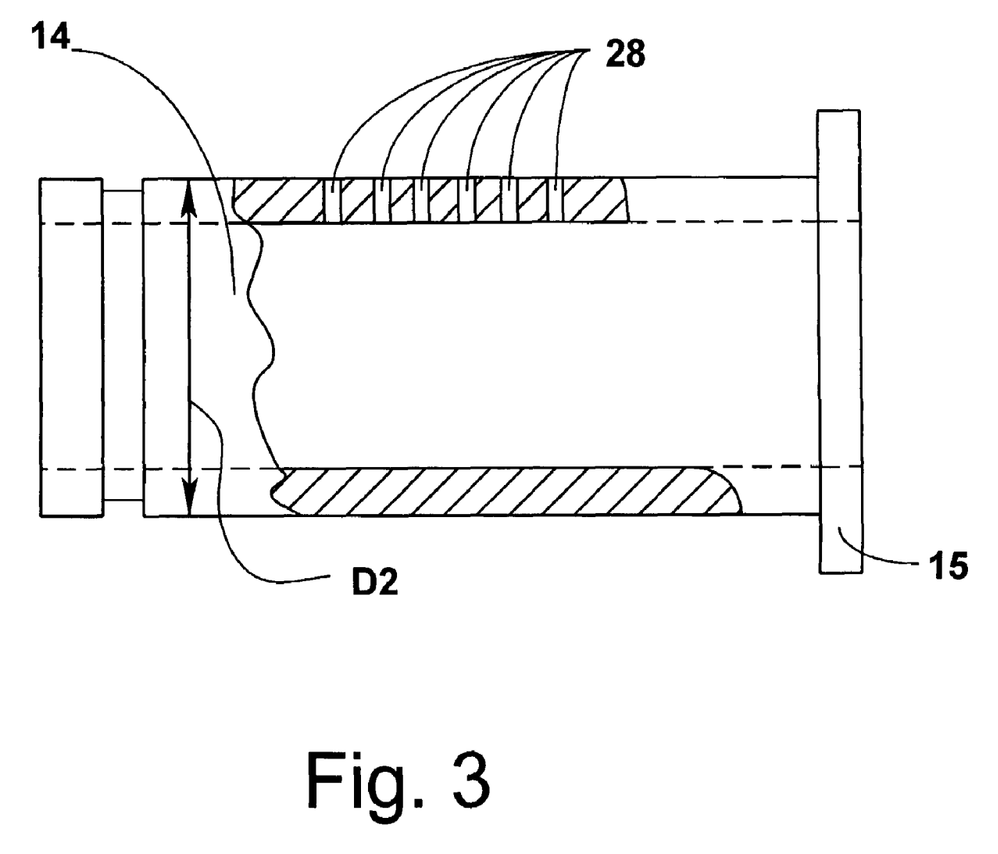
FIG. 3 is an elevation view of the side of a test cylinder constructed in accordance with the present invention.

Referring now to FIGS. 2 and 3: Test cylinder 14 is preferably constructed of a solid material such as acrylic. By way of example, in the preferred embodiment of the invention, the test cylinder 14 is 170 mm long, has outside diameter of 2.5 inches and an inside diameter of 1.75 inches. A cylinder collar 15, approximately 1.75 inches square by 0.25 inches thick, is attached to one end of the test cylinder 14. The inside surface 14a of the test cylinder 14 extends through the cylinder collar 15. The outside diameter D2 of test cylinder 14 is preferably sized so as to allow the outside (cylindrical) surface 14b of test cylinder 14 to slip fit inside of a corresponding opening 30 in a phantom body 32 (as will be described more fully herein below).

A matrix of holes 28 is located intermediately along test cylinder 14. In the preferred embodiment of the invention, each of the holes is radially oriented with respect to the longitudinal axis of test cylinder 14, although the holes 28 may, alternatively, be aligned parallel to each other. In the preferred embodiment of the invention, seven radially spaced apart rows of seven holes 28 each are counterbored into the wall of test cylinder 14 as shown in FIGS. 2 and 3. By way of example, in the preferred embodiment of the invention each hole 28 is approximately 1 mm diameter by 8.5 mm deep, so as each to accommodate a 1 mm by 5 mm steel fiducial 18 and adhesive (not shown). The seven rows of holes 18 are preferably radially spaced 5.0 degrees apart (center to center); and adjacent holes within each row are preferably spaced apart 5.0 mm (center to center).

Figures 4, 5:
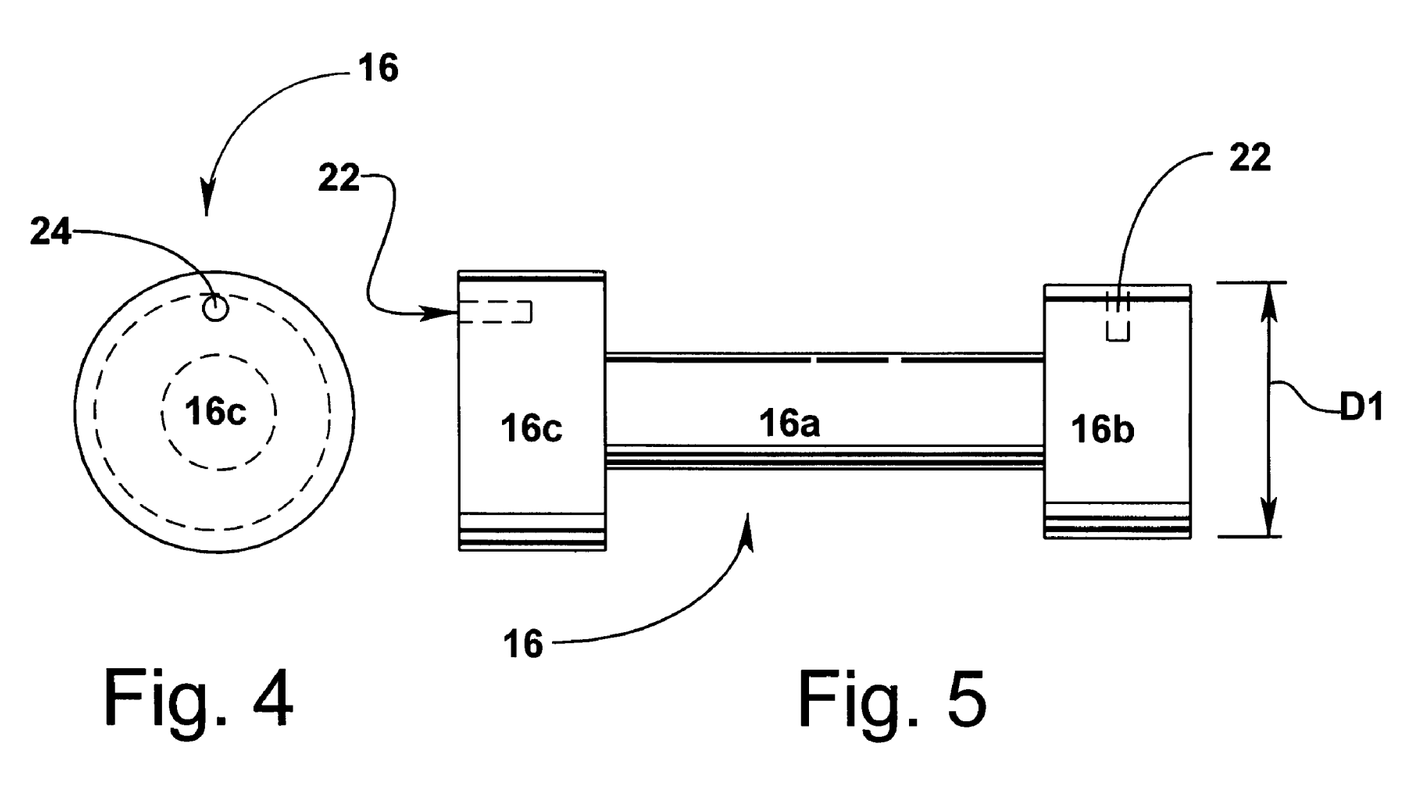
FIG. 4 is an elevation view of the front of a test rod constructed in accordance with the present invention.
FIG. 5 is an elevation view of the side of a test rod constructed in accordance with the present invention.

Referring now to FIGS. 4 and 5: Test rod 16 is preferably constructed of a solid material such as ABS, polyethylene or acrylic. By way of example, in the preferred embodiment of the invention, test rod 16 is 175 mm long and has a 30 mm diameter shaft 16a extending between a test rod distal shoulder 16b and a test rod proximal shoulder 16c. The test rod distal shoulder 16b is preferably 20 mm thick and has an outside diameter D1 that is sized so as to slip-fit into the inside surface 14a of the test cylinder 14. An approximately 1 mm diameter by approximately 5.5 mm deep hole 22 extends radially inwardly from the cylindrical surface of the test rod base 16b so as to accommodate a 1 mm diameter by 5 mm steel fiducial 20 and adhesive (not shown in FIG. 5). It will be understood that, in the preferred embodiment of the invention, the spaced-apart proximal shoulder 16c and distal shoulder 16b facilitate maintenance of alignment of text rod 16 inside of test cylinder 14.

A counterbored hole 24 is preferably provided in the end of test rod proximal shoulder 16c for attachment of test rod 16 to a motion actuator assembly 38.

Referring now to FIG. 6: In the preferred embodiment of the invention, the test apparatus sub-assembly 12 is designed to be used in conjunction with a dynamic phantom system (such as the one described in U.S. Pat. No. 7,151,253, which is included herein by reference thereto), comprising a tissue equivalent phantom body 32; a motion actuator assembly 38; and a motion controller assembly 40.

The tissue equivalent phantom body 32 is preferably secured to a phantom base member 33, which is preferably attached to an assembly base 34. The motion actuator assembly 38 is supported from the assembly base 34 by actuator support fixture 35.

Figure 7:
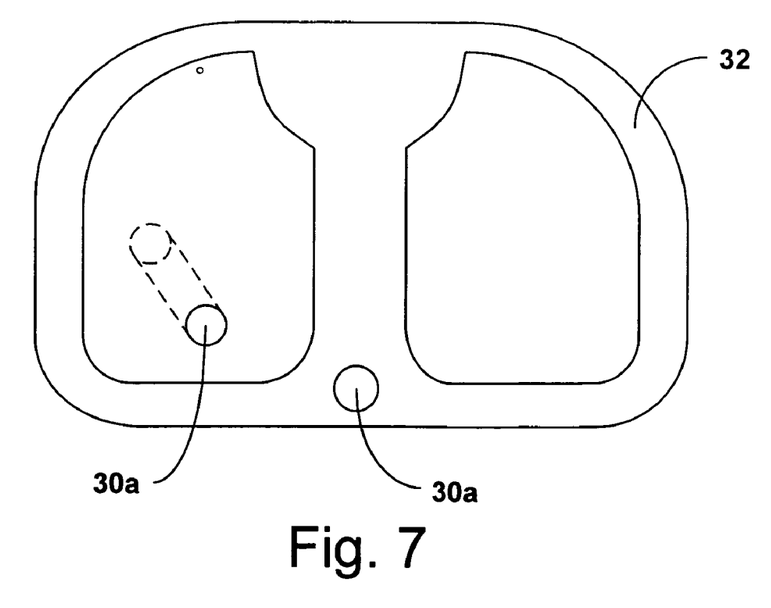
FIG. 7 is a front elevation view of a tissue equivalent phantom used in a preferred embodiment of the invention.
Figure 8:
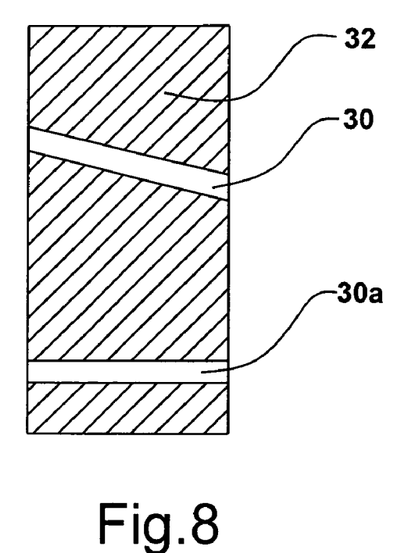
FIG. 8 is a cross-sectional view of the tissue equivalent phantom shown in FIG. 7; and, FIG. 9 is a perspective view of tissue equivalent phantom partially cut away to show the test apparatus sub-assembly.
Figure 9:
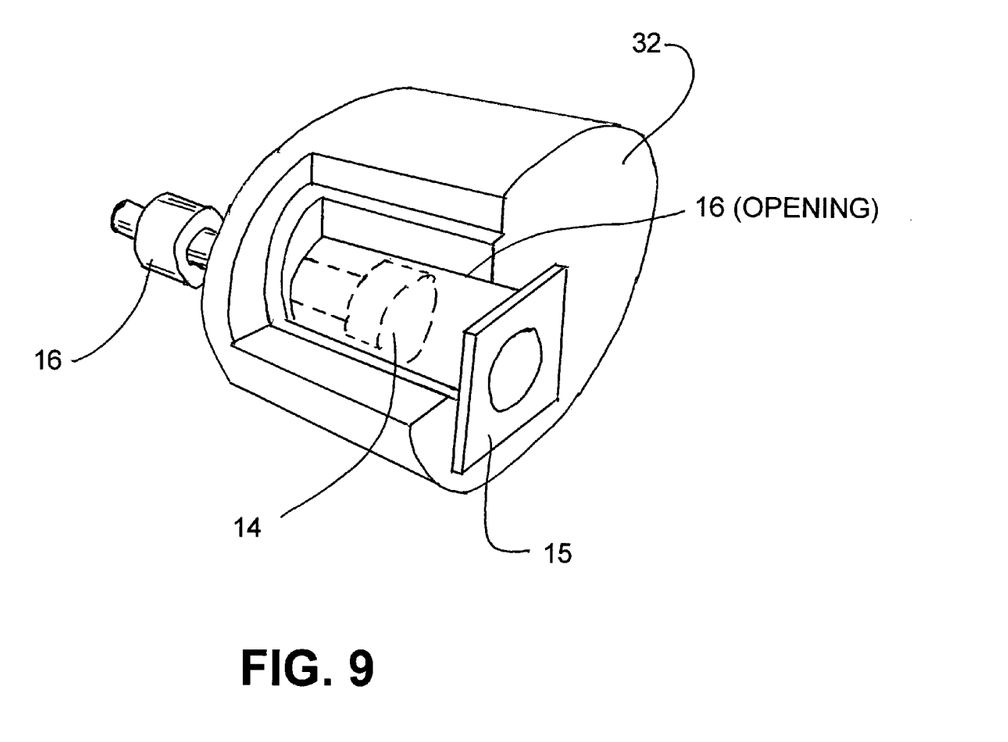

In the preferred embodiment of the invention, the tissue equivalent phantom body 32 is provided with a pair of through-holes 30 and 30a each of which is a diameter adapted to slideably receive the outside surface 14b of test cylinder 14. As described in referenced U.S. Pat. No. 7,151,253, one of the through holes 30 in the tissue equivalent phantom member 32 preferably runs longitudinally through the phantom approximately parallel to the axis of the phantom; and the other through hole 30a is preferably oriented not parallel to the axis of the phantom.

In the preferred embodiment of the present invention, motion actuator assembly 38 comprises a moveable actuator rod 42. Actuator rod 42 is attached, (for example, by threaded engagement) to test rod proximal shoulder 16c at counterbored hole 24. In operation, a motion controller assembly 40 electrically sends signals to motion actuator assembly 38, which causes actuator rod 42 to oscillate axially and/or rotationally, which causes test rod 16 to slideably move inside of test cylinder 14. As test rod 16 oscillates inside of test rod 16, moveable fiducial 20 inside of test rod 16 moves relative to static fiducials 18 inside of test cylinder 14.

In the preferred embodiment of the invention, cylinder collar 15 is in a plane perpendicular to the axis of cylinder 14, as shown in FIG. 3. The cylinder collar 15 provides a physical stop for proper insertion of the test apparatus sub-assembly 12 into opening 30 in phantom body 32. In alternative embodiments of the invention, cylinder collar 15 can be omitted.

Basic Operation:

An exemplary method of using the 4D CT QA device 10 to calibrate, confirm and/or test the accuracy of a motion-correlated CT system that acquires 3-dimensional image data is described. In response to predetermined signals from motion controller assembly 40, test rod 16 (and, therefore, fiducial 20) moves periodically (so as to mimic, for example, breathing motion) a known distance (excursion, displacement) relative to the static fiducials 18 at any given direction, for example anterior-posterior (AP), left-right (LR) and/or inferior-superior (IS) or rotationally.

The range of motion of test rod 16 is preferably set so that the location of moving fiducial 20 and the location of static fiducials 18 match at the maximum excursion of the test rod 16.

A motion-correlated 4D CT scanner may then acquire and sort images of the moving 4D CT QA device 10 at different motion phases. Zero percent and 50% phases should, preferably, each provide an image wherein the static and moving fiducials 18 and 20 are positioned next to each other.

Any difference observed and measured between the positions of the static and moving fiducials 18 and 20, on the static images generated by the 4D CT system, will be indicative of the accuracy (or lack thereof) of the 4D CT system's performance. Alternatively, if the range of motion of the test rod 16 is initially set up so that the positions of fiducials 18 and 20 do not match (i.e., are not in alignment with one another) at the maximum excursion, then the distance between the fiducials 18 and 20 can be measured in a static CT (without motion), and the generated images of the 4D CT phases should be evaluated against the known static position of the fiducials 18 and 20.

The above example describes a preferred embodiment of the invention that is particularly well suited for calibrating 4D CT systems. I should be understood, however, that modified embodiments of the invention are equally well suited for use in calibrating other medical imaging apparatus, including positron emission tomography (PET-CT), magnetic resonance imaging (MRI) and ultrasound imaging, Regardless of the nature of the imaging system that the present invention is to be used to calibrate, in each case the static fiducials 18 comprise discontinuities in the test cylinder 14; and the moveable fiducial 22 comprises a discontinuity in the test rod. Thus, for CT applications it is desirable that the fiducials 18 and 22, have different mass densities and/or radiopacity than that of the material of construction of test cylinder 14 and test rod 16; and, for MRI applications it is desirable that the fiducials 18 and 22, have different T1 and T2 values than that of the material of construction of test cylinder 14 and test rod 16, so that the magnetic resonance "signature" of the fiducials is distinctive from the test rod and test cylinder. For MRI applications, for example, the material of construction of test cylinder 14 and test rod 16 may be acrylic, and the fiducials 18 and 22 may be a paramagnetic material such as ferrous oxides, nickel chloride or copper sulfate.

While certain advantageous embodiments have been chosen to illustrate the invention, it will be understood by those skilled in the art that various changes and modifications can be made therein without departing from the scope of the invention. For example:

The test apparatus sub-assembly 12 can be used in conjunction with a motion actuator assembly, but without insertion of the sub-assembly 12 into a tissue equivalent phantom member (such as phantom body 32);

The tissue equivalent phantom body 32 can have one or more through holes (30, 30a) for receiving the test apparatus sub-assembly 12; and those holes may be oriented either parallel to or not parallel to a major axis of the phantom member;

The motion actuator assembly 38 may be designed to cause the actuator rod 42 (and, therefore, the test rod 16) to move axially or rotationally, or both;

In embodiments of the invention wherein the motion actuator assembly 38 doesn't cause the actuator rod 42 (and, therefore, the test rod 16) to move rotationally, the cross-sectional geometry of the test rod distal shoulder 16b, and the cross-sectional geometry of the inside surface 14a of the test cylinder, can each be of a shape other than circular, provided the two are substantially the same shape;

The number, size, spacing and shape of the holes 28 in the test cylinder 28 can be other than those described for the preferred embodiment of the invention;

The "fiducials" 18 and 20 that are inserted into the holes 28 and 22 in the test cylinder 14 and test rod 16, respectively, may be of any material having a density different from that of the test cylinder 14 and test rod 16;

The holes 28 and 22 in the test cylinder 14 and test rod 16, respectively, may alternatively be left empty, so that the "fiducials" comprise only air, which, being of a different density than that of the material of the test cylinder and test rod, may render the holes, themselves, as visible markers on static CT images of the apparatus;

The matrix of holes 28 (as well as the fixed fiducials 18 inserted therein) may be aligned so that their respective axes are parallel to each other, or, alternatively, so that their respective axes are each oriented radially with respect to the longitudinal axis of the test cylinder 14;

Use of the device 10 is not limited to use in conjunction with computed tomography (CT) systems, but may be used in a substantially similar manner to provide quality assurance data in other medical imaging systems, including PET, MRI and ultrasound systems;

Although the matrix of holes 28 comprise blind (i.e., counterbored) holes into which fiducials 18 may be inserted, the holes may alternatively be through-holes that extend from the outside surface 14b to the inside surface 14a of the test cylinder 14;

Various common attachment means, other than by threaded engagement at counterbored hole 24, may be used for connecting the proximal end of the test rod 16 to a motion actuator 38;

Means, such as treaded fasteners or pins extending, for example, through collar 15 may be provided in order to secure test cylinder 14 to phantom body 32;

The test rod 16 may be constructed without a distal shoulder 16b and proximal shoulder 16a, provided that the test geometry of the test rod conforms with (and slip fits with) the geometry of the inside surface 14b of the test cylinder in the proximity of the moveable fiducial 20; and, The material of construction of test rod 16 and test cylinder 14 may be other than ABS, polyethylene or acrylic, provided such material is substantially transparent to the imaging equipment (e.g., CT, PET, MRI, and ultrasound) that it is to be used to calibrate;

The fiducials 18, 20 may comprise a gas (i.e., air), a liquid, solid or gel material;

The fiducials 18, 20 may extend from the outside surfaces of the test cylinder 14 and test rod 16, respectively, or they may be imbedded inside the test cylinder 14 and test rod 16, respectively.

Accordingly, the scope of the invention should be determined not by the embodiments illustrated, but by the appended claims and their legal equivalents.

I claim:

1. A medical imaging quality assurance device, comprising:

a housing, said housing having a housing wall encircling a hollow interior chamber,
said interior chamber having a chamber longitudinal axis, and said chamber having a chamber cross-sectional geometry and area measurable perpendicular to said chamber longitudinal axis, and said chamber cross-sectional geometry and area being constant between two longitudinally spaced apart points;

a rod member having a proximal end portion and a distal end portion,
  said distal end portion of said rod member being slideably disposed inside of said interior chamber between said two longitudinally spaced apart points;

a first marker, said first marker being disposed in said distal end portion of said rod member, wherein said first marker comprises a discontinuity in said distal end portion of said rod member;

a plurality of second markers disposed in said wall of said housing, wherein each of said plurality of second markers comprises a discontinuity in said housing;

and means for attaching said proximal end portion of said rod member to a motion actuator.

2. The device according to claim 1,
wherein said plurality of second markers comprises at least two markers spaced apart and in a line parallel to said chamber axis.

3. The device according to claim 2,
wherein said first marker has a different mass density than a mass density of a material of construction of said distal end portion of said rod member;
and wherein each of said plurality of second markers has a different mass density than a mass density of a material of construction of said material of construction of said housing.

4. The device according to claim 3,
wherein said first marker further comprises an elongate member disposed in said distal end portion of said rod member;
and wherein each of said plurality of second markers further comprises an elongate member disposed in said housing wall.

5. The device according to claim 4,
wherein said rod member further comprises a shaft portion extending between said proximal end portion and said distal end portion;
and wherein said proximal end portion of said rod member is slideably disposed inside of said interior chamber.

6. The device according to claim 5, wherein said housing has a cylindrical outer surface.

7. The device according to claim 6, further comprising:
motion actuator means,
  wherein said motion actuator means comprise a motor and a motor output shaft,
  and wherein said motor output shaft is connected to said proximal end portion of said rod member.

8. The device according to claim 7, further comprising:
a tissue equivalent phantom member,
said phantom member having a first phantom opening extending through said phantom member;
and wherein said housing member is disposed within said first phantom opening.

9. The device according to claim 8, wherein said chamber cross-sectional geometry perpendicular to said chamber axis is circular.

10. The device according to claim 2,
wherein said first marker has a different mass density, radiopacity or magnetic resonance imaging signature than a respective mass density, radiopacity or magnetic resonance imaging signature of said material of construction of said distal end portion of said rod member;
and wherein each of said plurality of second markers has mass density, radiopacity or magnetic resonance imaging signature than a respective mass density, radiopacity or magnetic resonance imaging signature of said material of construction of said material of construction of said housing.

\* \* \* \* \*